(12) United States Patent
Morita

(10) Patent No.: US 10,194,883 B2
(45) Date of Patent: Feb. 5, 2019

(54) RADIOGRAPHIC IMAGING DEVICE AND METHOD

(71) Applicant: FUJIFILM Corporation, Tokyo (JP)

(72) Inventor: Junya Morita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/000,513

(22) Filed: Jun. 5, 2018

(65) Prior Publication Data

US 2018/0289353 A1    Oct. 11, 2018

Related U.S. Application Data

(63) Continuation of application No. 14/812,427, filed on Jul. 29, 2015, now Pat. No. 10,010,304, which is a
(Continued)

(30) Foreign Application Priority Data

Mar. 7, 2013    (JP) ................................ 2013-045009

(51) Int. Cl.
  *A61B 6/00*    (2006.01)
  *A61B 6/04*    (2006.01)
  *A61B 6/12*    (2006.01)

(52) U.S. Cl.
  CPC ............ *A61B 6/542* (2013.01); *A61B 6/0414* (2013.01); *A61B 6/12* (2013.01); *A61B 6/4035* (2013.01);
(Continued)

(58) Field of Classification Search
  None
  See application file for complete search history.

(56) References Cited

U.S. PATENT DOCUMENTS

| 2008/0226024 A1 | 9/2008 | Strommer | |
| 2011/0002519 A1* | 1/2011 | Tomisaki | A61B 6/12 382/131 |

(Continued)

FOREIGN PATENT DOCUMENTS

| JP | 2007-236804 A | 9/2007 |
| JP | 2009-507595 A | 2/2009 |

(Continued)

OTHER PUBLICATIONS

International Search Report, issued in PCT/JP2014/054366, dated Jun. 3, 2014.

(Continued)

*Primary Examiner* — Hoon K Song
(74) *Attorney, Agent, or Firm* — Birch, Stewart, Kolasch & Birch, LLP

(57) ABSTRACT

Disclosed are a radiographic imaging device and a radiographic imaging method which appropriately set an irradiation condition of radiation according to the presence or absence of an implant in a breast. An implant information acquisition unit 80 acquires implant information representing whether or not an implant is included in a breast M as a subject. An irradiation condition setting unit 82 sets, based on the implant information, a first irradiation condition C1 for irradiating the breast M with radiation when an implant is present and a second irradiation condition C2 for irradiating the breast M with radiation when an implant is absent. A radiation source drive control unit 70 drives an X-ray source 50 under the irradiation condition set by the irradiation condition setting unit 82 to irradiate the breast M with radiation.

20 Claims, 11 Drawing Sheets

Related U.S. Application Data continuation of application No. PCT/JP2014/054366, filed on Feb. 24, 2014.

(52) U.S. Cl.
CPC .............. *A61B 6/488* (2013.01); *A61B 6/502* (2013.01); *A61B 6/5211* (2013.01)

(56) References Cited

U.S. PATENT DOCUMENTS

| | | | |
|---|---|---|---|
| 2011/0058653 | A1 | 3/2011 | Baumgart et al. |
| 2013/0148782 | A1* | 6/2013 | Tajima ................... A61B 6/542 378/62 |

FOREIGN PATENT DOCUMENTS

| | | |
|---|---|---|
| JP | 2012-96084 A | 5/2012 |
| JP | 2012-170717 A | 9/2012 |
| JP | 2012-245228 A | 12/2012 |

OTHER PUBLICATIONS

Written Opinion of the International Searching Authority, issued in PCT/JP2014/054366, dated Jun. 3, 2014.

Japanese Office Action for corresponding Japanese Application No. 2013-045009, dated Apr. 5, 2016, with an English translation.

Non-Final Office Action from copending U.S. Appl. No. 14/812,427 dated Jan. 2, 2018.

Notice of Allowance from copending U.S. Appl. No. 14/812,427 dated May 9, 2018.

* cited by examiner

FIG. 6

FOR PRESENCE OF IMPLANT　　T1

| BREAST THICKNESS [mm] | T/F | TUBE VOLTAGE[kV] | TRANSMISSION DOSE |
|---|---|---|---|
| 20 | W/Rh | 27 | 0.7 |
| 30 | W/Rh | 29 | 1.2 |
| 40 | W/Rh | 31 | 2.1 |
| 50 | W/Rh | 33 | 3.5 |
| 60 | W/Rh | 35 | 7.0 |

FOR ABSENCE OF IMPLANT　　T2

| BREAST THICKNESS [mm] | T/F | TUBE VOLTAGE[kV] | TRANSMISSION DOSE |
|---|---|---|---|
| 20 | Mo/Mo | 25 | 0.6 |
| 30 | Mo/Mo | 27 | 1.0 |
| 40 | Mo/Mo | 29 | 1.6 |
| 50 | Mo/Rh | 31 | 2.6 |
| 60 | Mo/Rh | 33 | 4.0 |

RADIOGRAPHIC IMAGING DEVICE AND METHOD

CROSS-REFERENCE TO RELATED APPLICATIONS

This application is a Continuation of copending application Ser. No. 14/812,427 filed on Jul. 29, 2015, which is a Continuation of PCT International Application No. PCT/JP2014/054366 filed on Feb. 24, 2014, which claims priority under 35 U.S.C § 119(a) to Japanese Patent Application No. 2013-045009 filed on Mar. 7, 2013. The above applications are hereby expressly incorporated by reference, in their entirety, into the present application.

BACKGROUND OF THE INVENTION

1. Field of the Invention

The present invention relates to a radiographic imaging device and method which radiographs a subject, such as a breast, to acquire a radiographic image, and in particular, to a radiographic imaging device and method suitable for radiographing a breast including an implant.

2. Description of the Related Art

In recent years, in order to promote early detection of breast cancer, image diagnosis using a radiographic imaging device (called mammography) for radiographing a breast has attracted attention. A radiographic image (breast image) of the breast radiographed by the mammography is subjected to image processing in a dedicated operation terminal or the like, and is used for diagnosis by a physician. The physician examines the presence or absence of a lesion, such as tumor or calcification, by displaying the breast image on a display and reading the breast image.

In the mammography, in order to acquire a high-quality breast image, it is necessary to set an appropriate irradiation condition of radiation according to radiation transmittance of a breast as a subject. In particular, when a subject is a breast, transmittance of radiation is significantly different according to the thickness of the breast and the density of a mammary gland. For this reason, it is necessary to appropriately set the irradiation condition of a tube voltage and a tube current of a radiation source, an irradiation time, the type of a target generating radiation, the type of a filter capable of selectively absorbing a high energy component or a low energy component of radiation, and the like according to the state of the breast, thereby preventing the breast from being irradiated with excessive radiation.

As a method of setting the irradiation condition, a method (see JP2012-096084A) has been suggested, in which an automatic exposure control (AEC) sensor, which detects the dose of radiation transmitted through the breast, is provided in the mammography, the subject is irradiated with a small dose of radiation, the dose of transmitted radiation is detected by the AEC sensor, pre-irradiation is performed to set an irradiation condition necessary for radiographing, and then, main irradiation is performed to irradiate the subject with radiation under the set irradiation condition, thereby acquiring a radiographic image. A method (see JP2007-236804A) has also been suggested, in which an irradiation condition of main irradiation is set by analyzing a pre-radiographic image obtained through pre-irradiation.

On the other hand, for example, there is a case where breast reconstructive surgery after breast cancer surgery or breast enlargement surgery for beauty treatment is performed for a breast to be radiographed, and in this case, an implant, such as silicon or physiological saline, is embedded in the breast. In a breast embedded with an implant and a breast embedded with no implant, breast images acquired by radiographing are significantly different in image quality. In particular, the implant has a small dose of transmitted radiation, and appears as a high-luminance region in the breast image.

It is preferable that the irradiation condition at the time of radiographing of the breast is set to match the mammary gland as a region of interest to be diagnosed. Since the mammary gland has a comparatively small transmission amount of radiation, in many cases, the irradiation condition is set based on a region where the transmission amount of radiation is comparatively small. However, if an implant is embedded in the breast, the irradiation condition is set based on the region of the implant where the transmission amount of radiation is small, and as a result, the breast may be irradiated with excessive radiation.

For this reason, in the mammography, a method (see JP2009-507595A) has been suggested, in which a region where the transmission amount of radiation is extremely small is detected as an implant region, and irradiation condition is set excluding the detected implant region. According to the method of JP2009-507595A, an irradiation condition which is suitable when an implant is embedded in a breast are set, whereby, even if an implant is embedded in the breast, it is possible to prevent the breast from being irradiated with excessive radiation.

SUMMARY OF THE INVENTION

However, when the irradiation condition is set using the method described in JP2009-507595A excluding the implant region, the irradiation condition is set based on the region of the mammary gland having higher transmittance of radiation than the implant, and thus, radiation is hardly transmitted through the implant region. For this reason, the region of the implant in the breast image has very high luminance and becomes an overexposed image, and when a lesion exists in a portion overlapping the implant, it is not possible to confirm the lesion.

The invention has been accomplished in consideration of the above-described situation, and an object of the invention is to provide a radiographic imaging device capable of appropriately setting an irradiation condition of radiation according to whether or not an implant is included in a subject, and a radiographic imaging method capable of appropriately setting an irradiation condition according to whether or not an implant is included in a subject.

A radiographic imaging device according to the invention includes a radiation irradiation unit that irradiates a subject with radiation, a radiographic image acquisition unit that detects radiation transmitted through the subject to acquire a radiographic image, an implant information acquisition unit that acquires implant information representing whether or not an implant is included in the subject, and an irradiation condition setting unit that sets, based on implant information, any of a first irradiation condition of radiation for irradiating the subject when an implant is included in the subject and a second irradiation condition of radiation for irradiating the subject when an implant is not included in the subject. The radiation irradiation unit is an unit that irradiates the subject with radiation under the irradiation condition set by the irradiation condition setting unit.

In the radiographic imaging device according to the invention, the implant information acquisition unit may be an unit, before acquiring the radiographic image, that acquires the implant information based on a pre-radiographic image acquired by irradiating the subject with a smaller dose of radiation than the dose of radiation for irradiating the subject in case of acquiring the radiographic image.

The radiographic imaging device according to the invention may further include a selection unit that selects which irradiation condition of an irradiation condition matching the inside of an implant region and an irradiation condition matching the outside of the implant region is to be set with regard to the first irradiation condition.

In the radiographic imaging device according to the invention, the first and second irradiation conditions may include at least one of a combination of a target generating radiation in the radiation irradiation unit and a filter capable of absorbing a high energy component or a low energy component of radiation, a tube voltage of a radiation source in the radiation irradiation unit, a tube current of the radiation source, and an irradiation time of radiation.

In this case, the first irradiation condition may satisfy at least one of a condition that average energy is high, a condition that the irradiation time of radiation is short, and a condition that the irradiation dose of radiation determined by the tube voltage and the tube current is large, compared to the second irradiation condition.

The radiographic imaging device according to the invention may further include an information acquisition setting unit that sets whether or not to acquire the implant information by the implant information acquisition unit, and the irradiation condition setting unit may be an unit that sets a third irradiation condition when a setting for not acquiring the implant information is performed.

The third irradiation condition is an irradiation condition which is set without consideration of the presence or absence of an implant. The third irradiation condition is not necessarily different from the first and second irradiation conditions, and for example, in the case of a subject in which an implant is not included, the third irradiation condition may be the same as the second irradiation condition of radiation for irradiating the subject when an implant is absent.

A radiographic imaging method according to the invention, for irradiating a subject with radiation and detecting radiation transmitted through the subject to acquire a radiographic image of the subject, includes acquiring implant information representing whether or not an implant is included in the subject, setting, based on the implant information, any of a first irradiation condition of radiation for irradiating the subject when an implant is included in the subject and a second irradiation condition of radiation for irradiating the subject when an implant is not included in the subject, and irradiating the subject with radiation under the set irradiation condition.

According to the invention, it is possible to provide a radiographic imaging device capable of appropriately setting an irradiation condition of radiation according to whether or not an implant is included in a subject and a radiographic imaging method capable of appropriately setting an irradiation condition of radiation according to whether or not an implant is included in a subject.

BRIEF DESCRIPTION OF THE DRAWINGS

FIG. 6 is a diagram showing a dose table.

DESCRIPTION OF THE PREFERRED EMBODIMENTS

Figure 1:
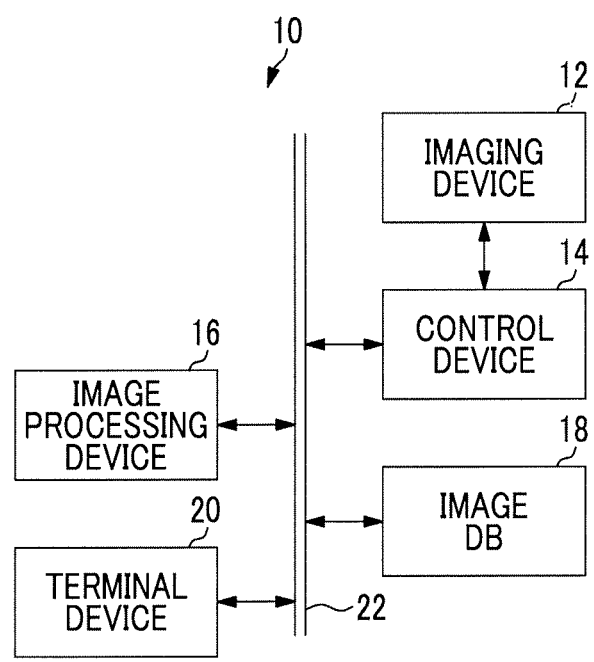
FIG. 1 is a schematic block diagram showing the configuration of a medical image support system including a radiographic imaging device according to a first embodiment.

An embodiment of the invention will be described referring to the drawings. FIG. 1 is a schematic block diagram showing the configuration of a medical image support system to which a radiographic imaging device according to a first embodiment of the invention is applied. As shown in FIG. 1, the system 10 includes a mammographic imaging device 12 which is installed in a medical facility or the like, a control device 14 which controls the mammographic imaging device 12, an image processing device 16 which performs image processing on a breast image radiographed by the mammographic imaging device 12, an image database (image DB) 18 which stores the breast image, and a terminal device 20 which has a high-definition monitor (not shown) and is carried by a physician who reads an image. The devices are connected to one another by a network 22. The mammographic imaging device 12 and the control device 14 constitute a radiographic imaging device of the invention.

Figure 2:
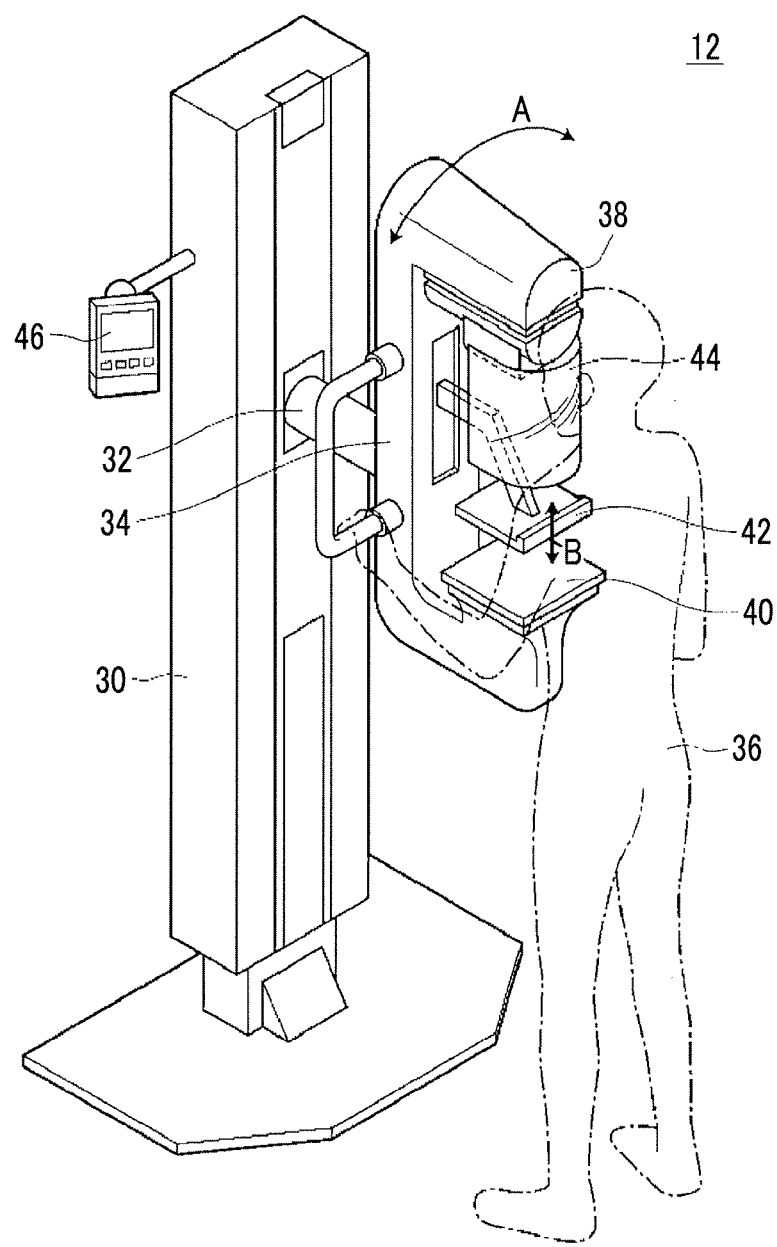
FIG. 2 is a schematic view showing the configuration of a mammographic imaging device.

FIG. 2 is a schematic view showing the configuration of the mammographic imaging device 12. As shown in FIG. 2, the mammographic imaging device 12 includes a base 30 which is provided in an erect state, an arm member 34 which is fixed to a pivot 32 arranged substantially at the central portion of the base 30, an X-ray source storage unit 38 which stores an X-ray source configured to expose radiation (X-rays) to a breast of a subject 36 and is fixed to one end portion of the arm member 34, a radiographing stand 40 which stores a solid-state detector configured to detect X-rays transmitted through the breast and to acquire a breast image, which is a radiographic image of the breast, and is fixed to the other end portion of the arm member 34, and a compression paddle 42 which compresses the breast to the radiographing stand 40.

The arm member 34, to which the X-ray source storage unit 38, the radiographing stand 40, and the compression paddle 42 are coupled, pivots about the pivot 32 in a direction of arrow A of FIG. 1, such that the radiographing direction to the breast of the subject 36 is adjustable. The compression paddle 42 is arranged between the X-ray source storage unit 38 and the radiographing stand 40 in a state coupled to the arm member 34, and is displaceable in a direction of arrow B of FIG. 1.

In the X-ray source storage unit 38, a face guard sheet 44 which is made of a member blocking X-rays is arranged in order to protect the vicinity of the face of the subject 36 from exposure of X-rays. In the base 30, a display 46 which displays radiographing information, such as a radiographing region and a radiographing direction of the subject 36, ID information of the subject 36, and, as necessary, information of a compression remaining time until the compression state of the breast by the compression paddle 42 is released is arranged.

Figure 3:
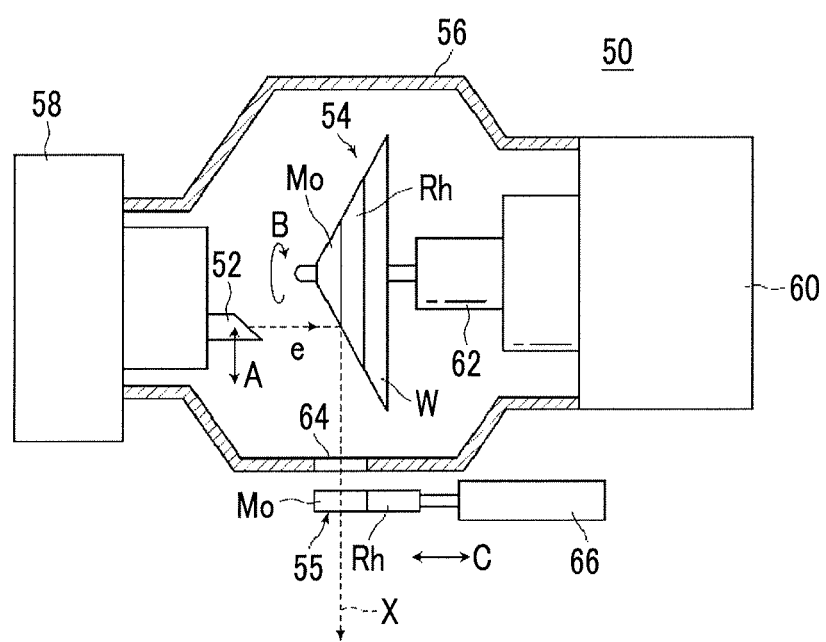
FIG. 3 is a schematic view showing the configuration of an X-ray source.

FIG. 3 is a schematic view showing the configuration of an X-ray source which is stored in the X-ray source storage unit 38. An X-ray source 50 includes a filament 52 which outputs an electron beam e, a target 54 which generates X-rays x when the electron beam e collides therewith, and a filter 55 which adjusts an energy spectrum of X-rays x. A predetermined tube voltage is applied between the filament 52 as a cathode and the target 54 as an anode under an irradiation condition set as described below. The filament 52 and the target 54 are stored in a vacuum envelope 56 which is filled with insulation oil. The filament 52 is held by a filament holder 58 arranged in one end portion of the vacuum envelope 56, and is movable in a direction of arrow A of FIG. 3. The target 54 is held by a target holder 60 arranged in the other end portion of the vacuum envelope 56 through a motor 62, and is rotatable in a direction of arrow B of FIG. 3.

In the target 54, a plurality of different anode substances, for example, Mo (molybdenum), Rh (rhodium), and W (tungsten) are arranged at different positions in a radial direction, and the incidence position of the electron beam e with respect to the target 54 can be switched by moving the filament 52 in the direction of arrow A of FIG. 3. With this, the energy spectrum of the X-rays x generated from the target 54 can be selected according to the anode substances.

The radiographing stand 40 is irradiated with X-rays x generated from the target 54 which are output through a radiation window 64 of Be formed in the vacuum envelope 56 and are transmitted through the filter 55. In the filter 55, a plurality of different substances, for example, Mo and Rh are arranged in a direction of arrow C of FIG. 3, and the filter 55 is moved in a direction of arrow C of FIG. 3 by a filter moving unit 66 such that a substance through which X-rays pass is selectable. As the substances forming the filter 55, in addition to the substances described above, Nb (niobium), Ag (silver), or a composite material of the simplexes thereof can be used.

Figure 4:
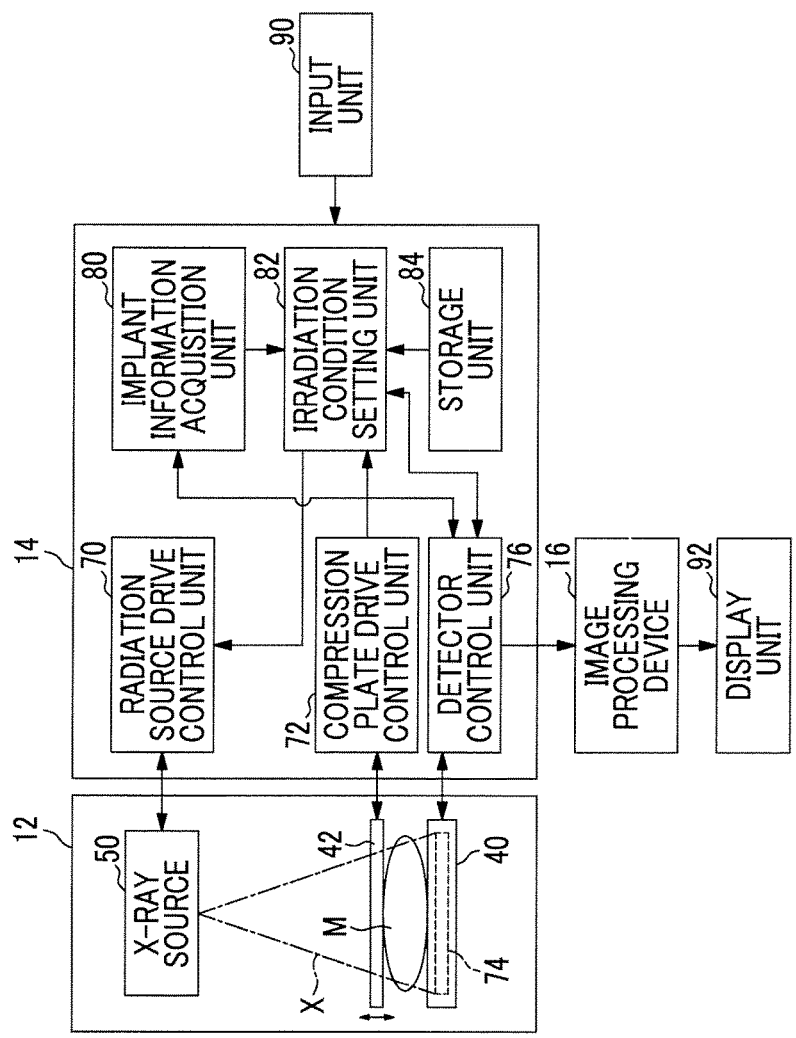
FIG. 4 is a block diagram of a control circuit constituting a mammographic imaging device and a control device in the first embodiment.

FIG. 4 is a block diagram of a control circuit constituting the mammographic imaging device and the control device in the first embodiment. The control device 14 which controls the mammographic imaging device 12 includes a radiation source drive control unit 70 which drives and controls the X-ray source 50 under a set irradiation condition, a compression paddle drive control unit 72 which drives and controls the compression paddle 42 and compresses a breast M of the subject 36 to the radiographing stand 40, a detector control unit 76 which controls the solid-state detector 74 stored in the radiographing stand 40 and acquires a radiographic image, an implant information acquisition unit 80 which acquires implant information representing whether or not an implant is included in the breast M, an irradiation condition setting unit 82 which sets an irradiation condition at the time of radiographing, and a storage unit 84 which stores various kinds of information including a dose table described below. An input unit 90 which performs various inputs to the control device 14 is connected to the control device 14. As the input unit 90, for example, in addition to a keyboard, a mouse, and the like, a touch panel, an operation button, and the like can be used.

The implant information acquisition unit 80, the irradiation condition setting unit 82, the storage unit 84, and the input unit 90 described above can be constituted of, for example, a computer system, such as a general personal computer.

The above-described irradiation condition is a condition for adjusting an energy spectrum (radiation quality) of X-rays for irradiating the breast M and obtaining a breast image having appropriate contrast, and includes, for example, the type of the target 54 constituting the X-ray source 50, the type of the filter 55, the tube voltage applied between the filament 52 and the target 54, and the irradiation dose (tube current x radiation irradiation time).

In this embodiment, before acquiring a breast image, pre-irradiation is performed on the breast M, implant information is acquired and the irradiation condition is set by analyzing a pre-radiographic image PG obtained through pre-irradiation, and main irradiation in which the breast M is irradiated with X-rays under the set irradiation condition to image a radiographic image is performed. It is assumed that radiographing of the breast M through pre-irradiation is referred to as pre-radiographing, and radiographing of the breast M through main irradiation is referred to as main radiographing. The dose of X-rays for irradiating the breast M in pre-radiographing is smaller than the dose of X-rays for irradiating the breast M in main radiographing.

Figure 5:
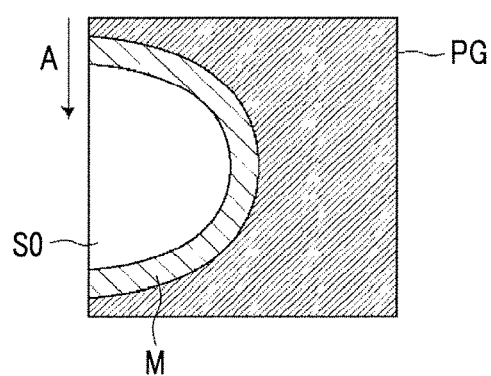
FIG. 5 is a diagram illustrating acquisition of implant information through analysis of a pre-radiographic image.

The implant information acquisition unit 80 analyzes the pre-radiographic image PG to acquire the implant information. FIG. 5 is a diagram illustrating a method of analyzing the pre-radiographic image PG to acquire the implant information. As shown in FIG. 5, the image of the breast M is included in the pre-radiographic image PG. An image of an implant is included in the image of the breast M. The implant information acquisition unit 80 acquires a profile of pixel values in a direction of arrow A parallel to the side to be a chest wall side in the pre-radiographic image. An implant embedded in the breast M has a small transmission dose of X-rays, appears as a high-luminance region S0 in the pre-radiographic image PG, and has a small amount of change in the direction of arrow A compared to change in pixel value of a mammary gland portion in the breast M. For this reason, for example, as described in JP2011-10884A, the implant information acquisition unit 80 acquires two profiles from the pre-radiographic image PG in the direction of arrow A, calculates a differential profile based on the two profiles, obtains a variation (standard deviation) in a range including the center of the differential profile based on the differential profile, and when the variation is equal to or less a threshold value, determines that an implant is included in the breast M.

A discriminator may be created by learning feature quantities, such as density and contrast, in multiple breast images, in which an implant region and a region with no implant are divided in advance, using a known machine learning method, a score representing implant likeness included in the pre-radiographic image PG may be calculated using the discriminator, and a region regarded as an implant may be recognized using a known region division method, such as a graph cut method. When the region regarded as an implant is equal to or greater than a predetermined ratio (for example, 10%) with respect to the region of the breast M in the pre-radiographic image PG, it may be determined that an implant is embedded in the breast M to be radiographed.

Before radiographing the breast M, in order to prevent damage to an implant due to compression, it is necessary to inquire to a patient about the presence or absence of an implant using an inquiry. For this reason, a technician may input the presence or absence of an implant based on the result of the inquiry from the input unit 90, and the implant information acquisition unit 80 may acquire implant information based on information of the presence or absence of an implant input by the technician. When acquiring a breast image in order to perform follow-up for the same patient, it is possible to confirm whether or not an implant is embedded for the same patient stored in the image database 18. For this reason, the implant information acquisition unit 80 may acquire implant information with reference to information of the same patient stored in the image database 18.

The irradiation condition setting unit 82 sets the irradiation condition of X-rays at the time of main radiographing of the breast M using the implant information. Hereinafter, the setting of the irradiation condition will be described. The irradiation condition setting unit 82 first calculates the thickness of the breast M based on positional information of the compression paddle 42 supplied from the compression paddle drive control unit 72. In this embodiment, a dose table for setting the irradiation condition is stored in the storage unit 84. FIG. 6 is a diagram showing the dose table. As shown in FIG. 6, in this embodiment, a dose table which is used when an implant is embedded in a subject, that is, a dose table T1 for the presence of an implant, and a dose table which is used when an implant is not embedded in a subject, that is, a dose table T2 for the absence of an implant, are stored in the storage unit 84. In the dose tables T1 and T2, a combination (T/F) of a target and a filter, a tube voltage (kV), and a transmission dose according to the thickness (mm) of the breast M are associated.

When the energy is higher, a subject transmission force of X-rays becomes stronger. The energy distribution of X-rays is determined by the combination of a target and a filter and the tube voltage of the X-ray source 50, and the average of the energy distribution is referred to as average energy. For example, when a target is made of W, the average energy of X-rays becomes higher compared to a case where a target is made of Mo. Furthermore, when a filter is made of Rh rather than Mo, the average energy of X-rays becomes higher, and when the tube voltage is higher, the average energy of X-rays becomes higher.

For this reason, in the dose table T1 for the presence of an implant, in order to increase the transmission force of X-rays in the breast M, the combination of a target and a filter, the tube voltage, and the transmission dose are set such that the breast M is irradiated with X-rays having higher average energy compared to the dose table T2 for the absence of an implant. Specifically, the irradiation condition of the dose table T1 sets higher energy at each thickness (mm) of the breast M than the irradiation condition of the dose table T2. With this, when an implant is present, that is, when an implant is included in the breast M, X-rays transmitted through the breast M reach the solid-state detector 74. On the contrary, in the dose table T2 for the absence of an implant, the combination of a target and a filter, the tube voltage, and the transmission dose are set such that the breast M is irradiated with X-rays having lower average energy compared to the dose table T1 for the presence of an implant.

When an implant is present, that is, when an implant is included in the breast M, the irradiation condition setting unit 82 sets the combination of a target and a filter, the tube voltage, the transmission dose as an irradiation condition based on the thickness of the breast M with reference to the dose table T1. For example, when the thickness of the breast M is 30 mm, W/Rh is set as the combination of a target and a filter, 29 kV is set as the tube voltage, and 1.2 is set as the transmission dose. When an implant is absent, that is, when an implant is not included in the breast M, the combination of a target and a filter, the tube voltage, and the transmission dose are set as an irradiation condition based on the thickness of the breast M with reference to the dose table T2. In the dose tables T1, T2, since the thickness of the breast M is defined discretely at an interval of 10 mm, the values of the tube voltage and the transmission dose at the thickness of the breast not defined in the dose tables T1 and T2 may be calculated through interpolation calculation using the values of the tube voltage and the transmission dose at the value of the contiguous thickness of the breast.

The irradiation condition setting unit 82 sets the tube current and the irradiation time for determining an irradiation dose (mAs) so as to become a set transmission dose as an irradiation condition using the analysis result of the pre-radiographic image PG. The irradiation condition setting unit 82 analyzes the above-described pre-radiographic image PG to set the tube current and the irradiation time. Specifically, the pre-radiographic image PG is analyzed to recognize an implant region, and a histogram of pixel values of a region excluding the implant region is created. A pixel region having a pixel value corresponding to a mammary gland in the histogram is extracted as a mammary gland region using the method described in JP2007-236804A, and the transmission dose of the mammary gland region is calculated from the pixel value of the mammary gland region and the irradiation dose at the time of pre-radiographing. When the implant region is recognized in the implant information acquisition unit 80, it is preferable that implant region information is acquired to analyze the pre-radiographic image. The irradiation dose at the time of main radiographing, that is, the tube current and the irradiation time, is set with reference to a table T3 (not shown) in which the difference between the transmission dose of the mammary gland region at the time of pre-radiographing and the transmission dose set with reference to the dose table T1 is associated with the irradiation dose (that is, the tube current and the irradiation time) at the time of main radiographing.

The irradiation dose is a value which is determined by the tube current (mA)×the irradiation time (sec). At the time of radiographing, it is preferable that the irradiation time of X-rays is set to be as short as possible to prevent blurring of a radiographic image due to body motion. In the mammography, although radiographing is performed while the breast is compressed by the compression paddle, in particular, when an implant is embedded in the breast M, in many cases, in order to prevent damage to an implant, radiographing is performed without compressing the breast M much. However, if radiographing is performed without compressing the breast M much, the breast image may be blurred due to body motion. For this reason, the table T3 sets the tube current and the irradiation time such that the irradiation time of X-rays becomes as short as possible, compared to the table which is used when an implant is absent. The set tube current and irradiation time are supplied to the radiation source drive control unit 70 as an irradiation condition C1 along with the combination of a target and a filter and the tube voltage.

When an implant is absent, a pixel region having a pixel value corresponding to a mammary gland in the histogram is extracted as a mammary gland region, and the transmission dose of the mammary gland region is calculated from the pixel value of the mammary gland region and the irradiation dose at the time of pre-radiographing. The tube current and the irradiation time at the time of main radiographing are set with reference to a table T4 (not shown) in which the difference between the transmission dose of the mammary gland region at the time of pre-radiographing and the transmission dose set with reference to the dose table T2 is associated with the irradiation dose (that is, the tube current and the irradiation time) at the time of main radiographing. The set tube current and irradiation time are supplied to the radiation source drive control unit 70 as an irradiation condition C2 along with the combination of a target and a filter and the tube voltage. The tables T3 and T4 are stored in the storage unit 84.

Since the irradiation condition C1 when an implant is present is set such that X-rays having higher average energy are irradiated compared to the irradiation condition C2 when an implant is absent, X-rays are transmitted through the implant region and are detected by the solid-state detector 74. For this reason, it is possible to observe a tissue which overlaps an implant in a breast image acquired through main radiographing.

It is preferable that an exposure dose to the breast M is equal when an implant is included in a subject and when an implant is not included in a subject. However, in order to further facilitate observation of a tissue in a region overlapping an implant, the irradiation condition C1 when an implant is included in a subject may be set to have a greater irradiation dose than the irradiation condition C2 when an implant is not included in a subject. For example, the irradiation condition C1 may be set so as to be 1.2 times the irradiation condition C2.

In the irradiation condition setting unit 82, as described in JP2012-096084A, an AEC sensor may be provided in the mammographic imaging device 12, and the irradiation conditions C1 and C2 may be set using the detection result of the AEC sensor, instead of the pre-radiographic image PG.

The image processing device 16 performs image processing on a breast image acquired through main radiographing under a predetermined image processing condition. The image processing condition includes, for example, a standardization processing condition of a radiographic image, a frequency processing condition, a noise filtering processing condition, a dynamic range adjustment processing condition, a gradation processing condition, or the like. A display unit 92, such as a liquid crystal display, is connected to the image processing device 16, and a processed radiographic image is displayed on the display unit 92 to enable confirmation of an image.

Figure 7:
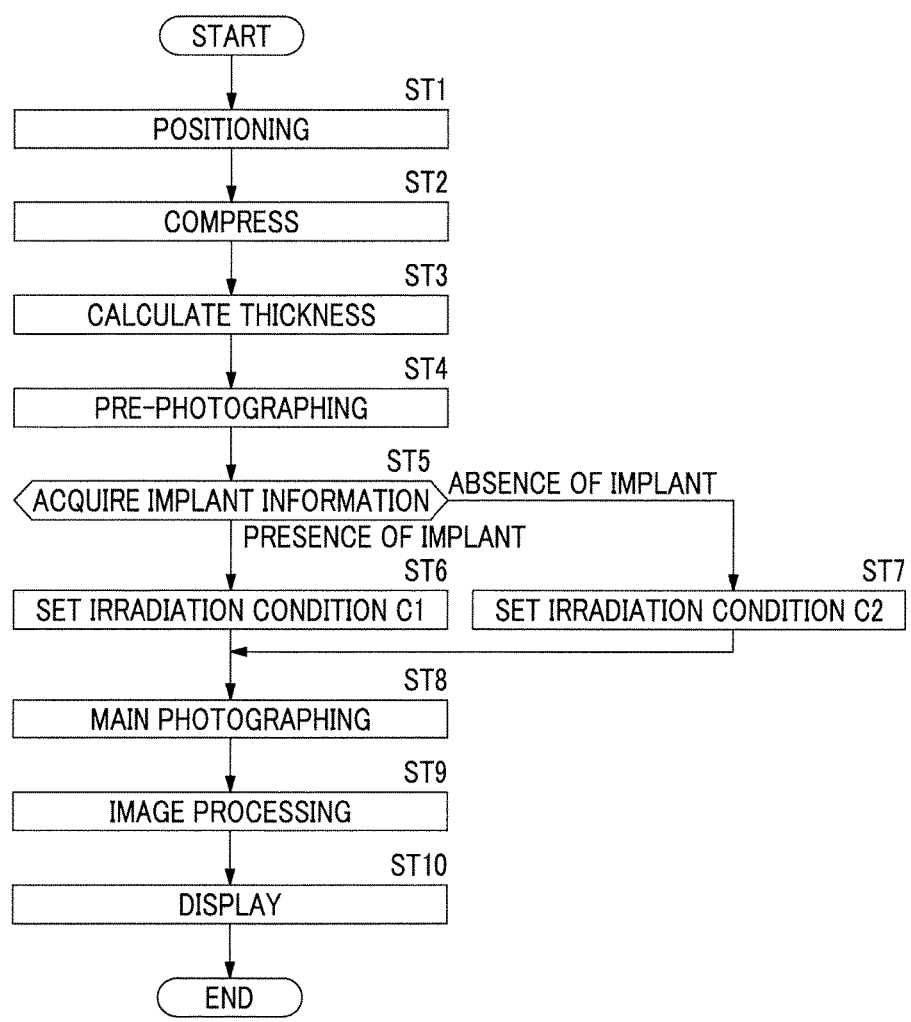
FIG. 7 is a flowchart showing processing which is performed in the first embodiment.

Next, processing which is performed in the first embodiment will be described. FIG. 7 is a flowchart showing processing which is performed in the first embodiment. The technician positions the breast M with respect to the radiographing stand 40 of the mammographic imaging device 12 (Step ST1), and moves the compression paddle 42 using the compression paddle drive control unit 72 to compress the breast M (Step ST2). When the breast M is compressed in a desired state, the movement of the compression paddle 42 is stopped, and the thickness of the breast M at this time is calculated by the irradiation condition setting unit 82 (Step ST3). The irradiation condition setting unit 82 acquires positional information of the compression paddle 42 with respect to the radiographing stand 40 from the compression paddle drive control unit 72, and calculates the thickness of the breast M from the positional information. Information of the calculated thickness is displayed on the display 46.

Next, the setting of pre-radiographing is performed by the technician for the mammographic imaging device 12, and if a radiographing switch (not shown) is turned on, the radiation source drive control unit 70 drives the X-ray source 50 and irradiates the breast M with X-rays under the irradiation condition of pre-radiographing to perform pre-radiographing of the breast M (Step ST4). The pre-radiographic image PG of the breast M recorded in the solid-state detector 74 through the radiographing is read by the detector control unit 76 and is supplied to the control device 14.

The implant information acquisition unit 80 of the control device 14 analyzes the pre-radiographic image PG to acquire implant information representing the presence or absence of an implant in the breast M (Step ST5). Next, the irradiation condition setting unit 82 sets the irradiation condition at the time of main radiographing based on the implant information. That is, when the implant information represents the presence of an implant, the irradiation condition C1 for the presence of an implant is set based on the dose table T1 and the analysis result of the pre-radiographic image PG (Step ST6). When the implant information represents the absence of an implant, the irradiation condition C2 for the absence of an implant is set based on the dose table T2 and the analysis result of the pre-radiographic image PG (Step ST7). The set irradiation conditions C1 and C2 are supplied to the radiation source drive control unit 70.

The radiation source drive control unit 70 moves the filament 52 in the direction of arrow A of FIG. 3 under the set irradiation condition and selects the target 54. The radiation source drive control unit 70 drives the filter moving unit 66 to move the filter 55 in the direction of arrow C of FIG. 3 under the set irradiation condition and selects the filter 55.

Next, if the radiographing switch (not shown) is turned on by the technician, the radiation source drive control unit 70 drives the X-ray source 50 to irradiate the breast M with X-rays under the set irradiation condition, thereby performing main radiographing of the breast M (Step ST8). A breast image which is a radiographic image of the breast M recorded in the solid-state detector 74 through the radiographing is read by the detector control unit 76 and is supplied to the image processing device 16.

The image processing device 16 performs image processing on the breast image under a predetermined image processing condition and acquires a processed radiographic image (Step ST9). That is, the breast image is analyzed to set the standardization processing condition, the frequency processing condition, the noise filtering processing condition, the dynamic range adjustment processing condition, and the gradation processing condition of the breast image. Image processing is performed on the breast image under the set image processing condition. When the irradiation condition C1 for the presence of an implant is set, X-rays have high energy; thus, contrast of the breast image is degraded. For this reason, when the irradiation condition C1 is set, it is preferable to set the gradation processing condition and the frequency processing condition in order to increase contrast.

The breast image subjected to the image processing in the above-described manner is displayed on the display unit 92, confirmation by the technician is performed (Step ST10), and the processing ends.

In this way, in the first embodiment, based on the implant information, the irradiation condition C1 for the presence of an implant is set when an implant is present, and the irradiation condition C2 for the absence of an implant is set when an implant is absent. For this reason, it is possible to appropriately set the irradiation condition of X-rays according to the presence or absence of an implant in the breast M.

Since the implant information is acquired based on the pre-radiographic image PG, it is possible to accurately acquire the implant information, and thus, to more appropriately set the irradiation condition of X-rays at the time of main radiographing.

Next, a second embodiment of the invention will be described. In a medical image support system to which a radiographic imaging device of the second embodiment is applied, only the configuration of a control device is different from that in the first embodiment; thus, detailed description of the configuration of the medical image support system will not be repeated.

Figure 8:
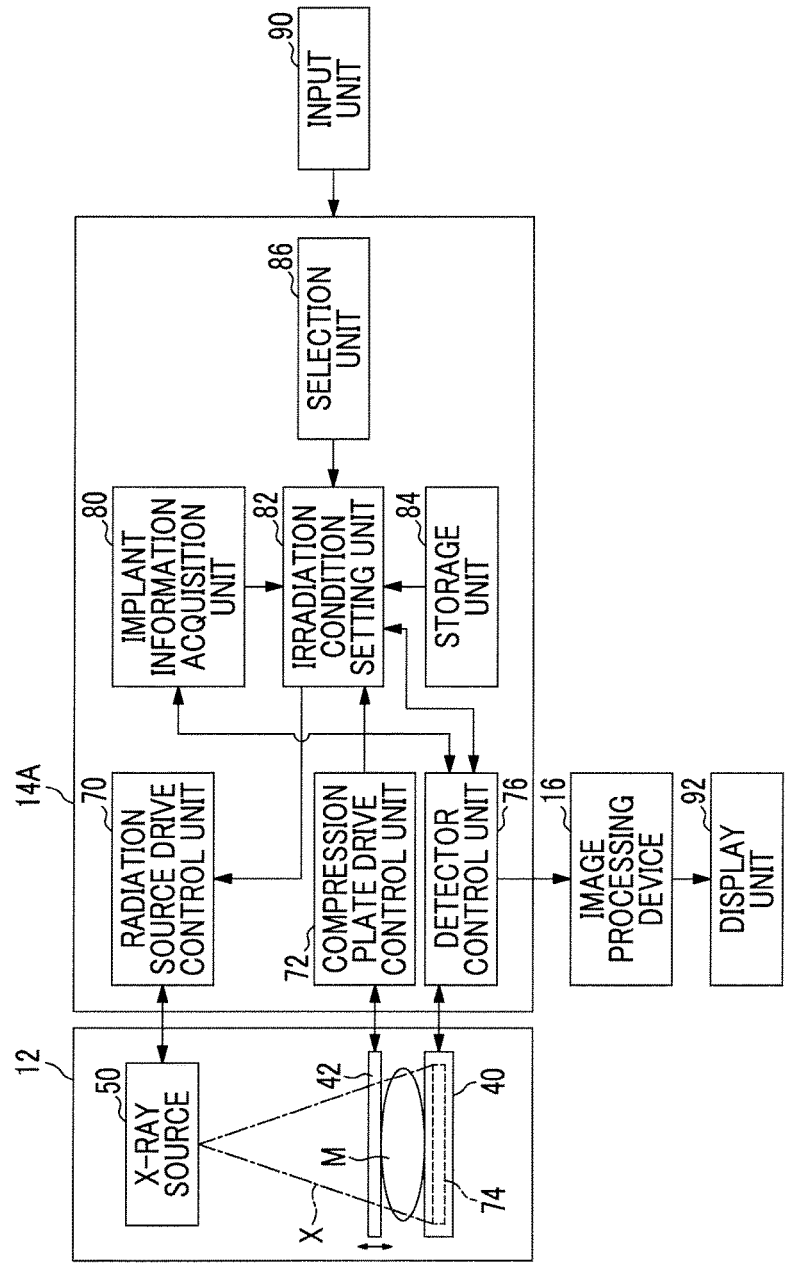
FIG. 8 is a block diagram of a control circuit constituting a mammographic imaging device and a control device in a second embodiment.

FIG. 8 is a block diagram of a control circuit constituting a mammographic imaging device and a control device in the second embodiment. In the second embodiment, the same configurations as those in the first embodiment are represented by the same reference numerals, and detailed description thereof will not be repeated. The second embodiment is different from the first embodiment in that a control device 14A is provided with a selection unit 86 which selects whether to set an irradiation condition matching the inside of an implant region or to set an irradiation condition matching the outside of an implant region with regard to the irradiation condition C1 for the presence of an implant according to an instruction from the input unit 90.

In the above-described first embodiment, when an implant is present, the irradiation condition C1 is set based on the analysis result of the mammary gland region in the pre-radiographic image PG and the dose table T1; thus, it is possible to observe a tissue for an implant region in the breast image acquired through main radiographing. However, there is a case where it is desired to observe a lesion or the like overlapping the implant region in more detail.

For this reason, in the second embodiment, the selection unit 86 selects whether to set an irradiation condition matching the outside of the implant region or to set an irradiation condition matching the inside of the implant region by an input of the technician from the input unit 90.

When the selection unit 86 selects to set an irradiation condition, as in the foregoing first embodiment, the irradiation condition setting unit 82 sets an irradiation condition (represented by C1-1) matching the outside of the implant region based on the dose table T1 and the analysis result of the mammary gland region in the pre-radiographic image PG.

When the selection unit 86 selects to set an irradiation condition matching the inside of the implant region, an irradiation condition (represented by C1-2) matching the inside of the implant region is set based on the dose table T1 and the analysis result of the implant region in the pre-radiographic image PG. Specifically, a histogram of the pre-radiographic image PG is created, a pixel region having a pixel value corresponding to an implant in the histogram is extracted as an implant region, and the transmission dose of the implant region is calculated based on the pixel value of the implant region and the irradiation dose at the time of pre-radiographing. The irradiation dose at the time of main radiographing, that is, the tube current and the irradiation time, is set with reference to a table T5 in which the difference between the transmission dose of the implant region at the time of pre-radiographing and the transmission dose set with reference to the dose table T1 is associated with the irradiation dose at the time of main radiographing. The table T5 is created in advance and is stored in the storage unit 84 in order to set an irradiation condition matching the inside of the implant region.

Figure 9:
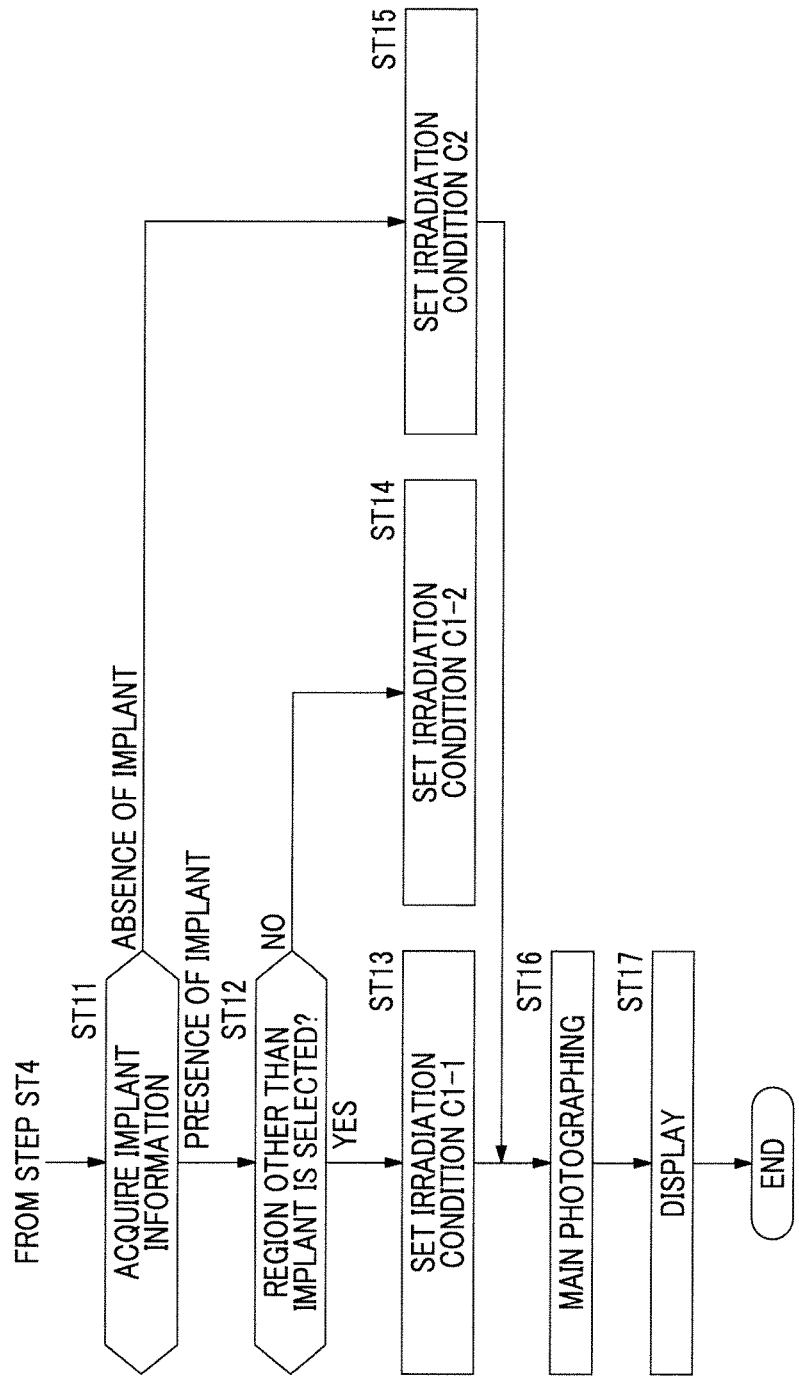
FIG. 9 is a flowchart showing processing which is performed in the second embodiment.

Next, processing which is performed in the second embodiment will be described. FIG. 9 is a flowchart showing processing which is performed in the second embodiment. In the second embodiment, only processing after Step ST5 in the flowchart of the first embodiment is different; thus, only the processing after Step ST5 will be described.

Subsequently to Step ST4 of the first embodiment, if the implant information acquisition unit 80 acquires the implant information representing the presence of an implant (Step ST11), the irradiation condition setting unit 82 determines whether or not the setting of an irradiation condition based on a region outside an implant is selected by the selection unit 86 (Step ST12). If Step ST12 is affirmative, the irradiation condition setting unit 82 sets the irradiation condition C1-1 matching the outside of the implant region based on the dose table T1 and the analysis result of the mammary gland region in the pre-radiographic image PG (Step ST13). If Step ST12 is negative, the irradiation condition setting unit 82 sets the irradiation condition C1-2 matching the inside of the implant region based on the dose table T1 and the analysis result of the implant region in the pre-radiographic image PG (Step ST14).

When the implant information represents the absence of an implant, the irradiation condition C2 for the absence of an implant is set based on the dose table T2 and the analysis result of the pre-radiographic image PG (Step ST15).

The set irradiation condition is supplied to the radiation source drive control unit 70. The radiation source drive control unit 70 moves the filament 52 in the direction of arrow A of FIG. 3 under the set irradiation condition and selects the target 54. The radiation source drive control unit 70 drives the filter moving unit 66 under the set irradiation condition to move the filter 55 in the direction of arrow C of FIG. 3 and selects the filter 55. Next, if the radiographing switch (not shown) is turned on by the technician, the radiation source drive control unit 70 drives the X-ray source 50 to irradiate the breast M with X-rays under the set irradiation condition, thereby performing main radiographing (Step ST16). A breast image which is a radiographic image of the breast M recorded in the solid-state detector 74 through the radiographing is read by the detector control unit 76 and is supplied to the image processing device 16. The image processing device 16 performs image processing on the breast image under a predetermined image processing condition and acquires a processed radiographic image (Step ST17). The breast image subjected to the image processing in the above-described manner is displayed on the display unit 92, confirmation by the technician is performed (Step ST18), and the processing ends.

In this way, in the second embodiment, when an implant is included in the breast M, the selection regarding whether to acquire the irradiation condition C1-1 matching the outside of the implant region or to acquire the irradiation condition C1-2 matching the inside of the implant region is received. For this reason, it is possible to cope with a case where it is desired to perform observation of a region overlapping an implant and a case where it is desired to perform observation of a region other than a region overlapping an implant.

Next, a third embodiment of the invention will be described. In a medical image support system to which a radiographic imaging device of the third embodiment is applied, only the configuration of a control device is different from that in the first embodiment; thus, detailed description of the configuration of the medical image support system will not be repeated.

Figure 10:
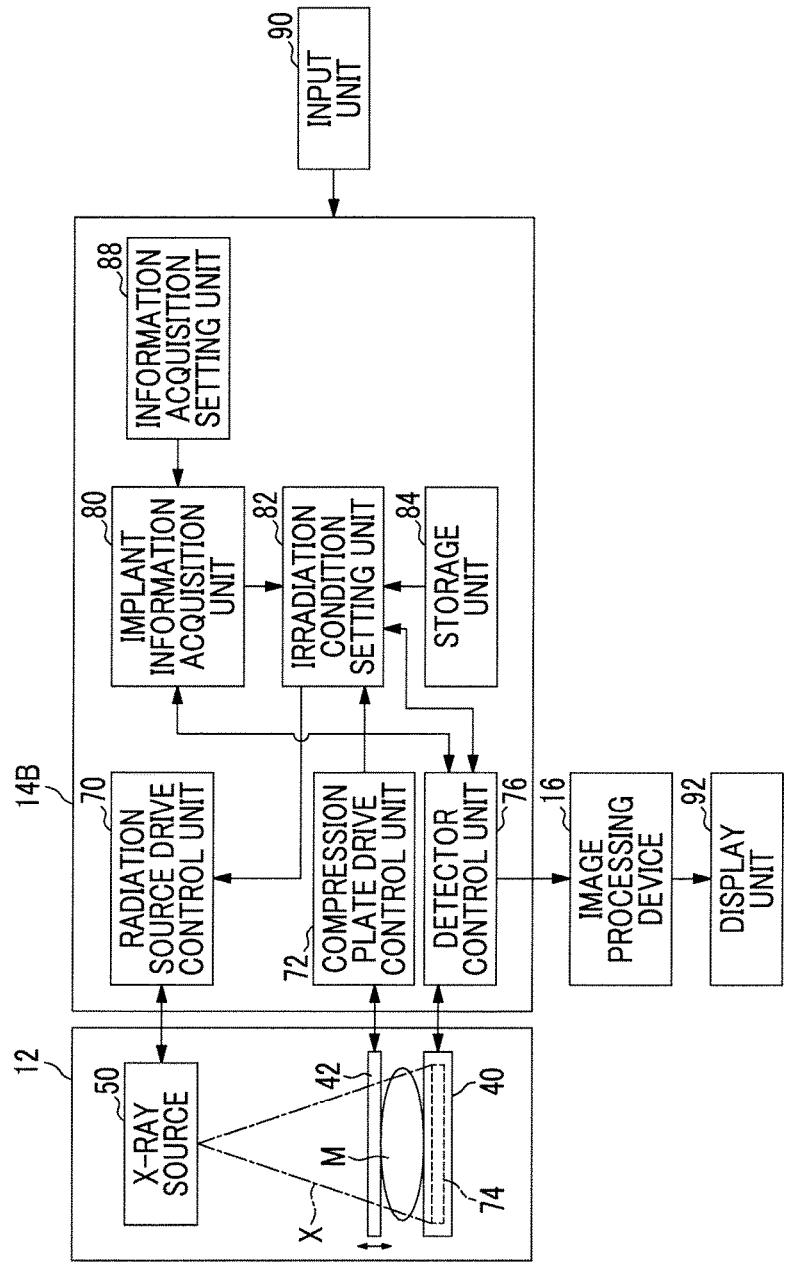
FIG. 10 is a block diagram showing a control circuit constituting a mammographic imaging device and a control device in a third embodiment.

FIG. 10 is a block diagram of a control circuit constituting a mammographic imaging device and a control device in the third embodiment. In the third embodiment, the same configurations as those in the first embodiment are represented by the same reference numerals, and detailed description thereof will not be repeated.

In the above-described first embodiment, the implant information acquisition unit 80 acquires the implant information representing the presence or absence of an implant, and the irradiation conditions C1 and C2 are set using the implant information. However, it is difficult to accurately recognize the implant region of the breast M 100% depending on accuracy of recognition of the implant region. A mammary gland region included in the breast M embedded with no implant may be erroneously recognized as an implant. In this way, when an implant region cannot be accurately recognized, it is not possible to appropriately set an irradiation condition; thus, it is preferable to set an irradiation condition without using implant information. In particular, when an irradiation condition is not appropriately set, and image quality of an acquired breast image is not satisfactory, it is necessary to perform re-radiographing; however, in this case, it is not preferable to set an irradiation condition again using implant information.

The third embodiment is different from the first embodiment in that a control device 14B is further provided with an information acquisition setting unit 88 which sets whether or not to acquire implant information in the implant information acquisition unit 80 by an input from the input unit 90, and when the setting not to acquire implant information is performed, the irradiation condition setting unit 82 sets an irradiation condition of main radiographing based on only the analysis result of the pre-radiographic image PG without using implant information.

Figure 11:
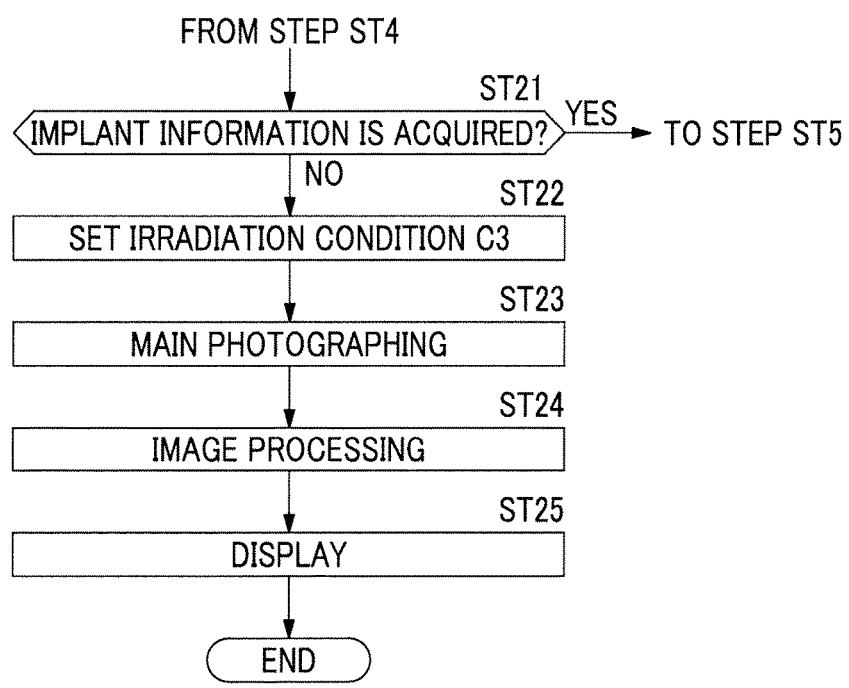
FIG. 11 is a flowchart showing processing which is performed in the third embodiment.

Next, processing which is performed in the third embodiment will be described. FIG. 11 is a flowchart showing processing which is performed in the third embodiment. In the third embodiment, only processing after Step ST5 in the flowchart of the first embodiment is different; thus, only the processing after Step ST5 will be described.

Subsequently to Step ST4 of the first embodiment, the implant information acquisition unit 80 determines whether or not the acquisition of implant information is set by the information acquisition setting unit 88 (Step ST21). If Step ST21 is affirmative, the process progresses to Step ST5 in the first embodiment. The processing after Step ST5 is the same as in the first embodiment; thus detailed description thereof will not be repeated.

If Step ST21 is negative, the irradiation condition setting unit 82 sets an irradiation condition C3 without using implant information (Step ST22). Specifically, the pre-radiographic image PG is analyzed, and the irradiation condition C3 is set based on the pixel value of the mammary gland region in the pre-radiographic image PG with reference to a dose table in which the combination of a target and a filter, the tube voltage, and the transmission dose according to the thickness of the breast M are associated. In the analysis of the pre-radiographic image PG, the recognition of the implant region is not performed, and the pixel value of the mammary gland region is calculated without consideration of the presence or absence of an implant. As the dose table, the dose table T2 for the absence of an implant in the above-described first embodiment may be used. When the dose table T2 is used, the irradiation condition C3 is the same as the irradiation condition C2. A dose table which is prepared for a case where implant information is not used may be used. The set irradiation condition is supplied to the radiation source drive control unit 70.

The radiation source drive control unit 70 moves the filament 52 in the direction of arrow A of FIG. 3 under the set irradiation condition C3 and selects the target 54. The radiation source drive control unit 70 drives the filter moving unit 66 under the set irradiation condition to move the filter 55 in the direction of arrow C of FIG. 3 and selects the filter 55. Next, if the radiographing switch (not shown) is turned on by the technician, the radiation source drive control unit 70 drives the X-ray source 50 to irradiate the breast M with X-rays under the set irradiation condition, thereby performing main radiographing (Step ST23). A breast image which is a radiographic image of the breast M recorded in the solid-state detector 74 through the radiographing is read by the detector control unit 76 and is supplied to the image processing device 16. The image processing device 16 performs image processing on the breast image under a predetermined image processing condition and acquires a processed radiographic image (Step ST24). The breast image subjected to the image processing in the above-described manner is displayed on the display unit 92, confirmation by the technician is performed (Step ST25), and the processing ends.

In this way, in the third embodiment, when the setting not to acquire implant information is performed, the irradiation condition C3 is set without using implant information; thus, it is possible to prevent erroneous recognition of the implant region and to appropriately set the irradiation condition of main radiographing.

In the above-described third embodiment, although the information acquisition setting unit 88 is provided in the control device of the first embodiment, the information acquisition setting unit 88 may be provided in the control device of the second embodiment. In this case, when the setting to acquire implant information is performed, the processing after Step ST11 in the second embodiment is performed, and any one of the irradiation conditions C1-1, C1-2, and C2 is set.

In the above-described embodiments, although a breast is a subject, the invention is not limited thereto, and an arbitrary region, such as a chest, an abdomen, a head, or a limb of a human body, may be a subject. In this case, when any implant is embedded inside a human body, similarly to the embodiments of the invention described above, an irradiation condition in consideration of an implant region is set.

In the above-described embodiments, although all of the combination of a target and a filter, the tube voltage, the tube current, and the irradiation time are designated and set as an irradiation condition, at least one of the combination of a target and a filter, the tube voltage, the tube current, and the irradiation time may be set as an irradiation condition.

The invention is not limited to the above-described example, and various improvements or modifications may be made without departing from the spirit and scope of the invention.

Hereinafter, the functional effects of the dependent claims of the invention will be described.

It is possible to accurately acquire the implant information by acquiring the implant information based on pre-irradiation, and thus, to more appropriately set the irradiation condition of radiation.

The selection of any of the irradiation condition matching the inside of the implant region and the irradiation condition matching the outside of the implant region is received with regard to the first irradiation condition, whereby it is possible to cope with a case where it is desired to intensively perform observation of a region overlapping an implant and a case where it is desired to intensively perform observation of a region other than a region overlapping an implant.

The section regarding whether or not to acquire implant information is received, and when the selection not to acquire implant information is performed, the third irradiation condition is set, whereby it is possible to prevent erroneous recognition as the presence of an implant for a subject including no implant, and to more appropriately set the irradiation condition of radiation.

What is claimed is:

1. A radiographic imaging device comprising:
   a radiation irradiation unit that irradiates a breast as a subject with radiation;
   a radiographic image acquisition unit that detects radiation transmitted through the breast to acquire a radiographic image of the breast; and
   an irradiation condition setting unit that sets an irradiation condition of radiation for irradiating the breast in acquiring the radiographic image,
   wherein the irradiation condition setting unit
   calculates a thickness of the breast,
   calculates a transmission dose based on the calculated thickness of the breast with reference to a dose table for setting the transmission dose according to the thickness of the breast,
   analyzes a pre-radiographic image acquired by performing pre-radiographing for irradiating the breast with a small dose of radiation, before the radiographic image is acquired by irradiating the breast with radiation under the irradiation condition set by the irradiation condition setting unit, to recognize an implant region corresponding to an implant included in the breast in the pre-radiographic image,
   extracts a mammary gland region from a region excluding the implant region in the pre-radiographic image,
   calculates a transmission dose of the mammary gland region at the time of the pre-radiographing from a pixel value of the mammary gland region, and
   sets the irradiation condition based on the difference between the transmission dose of the mammary gland region at the time of the pre-radiographing and the calculated transmission dose with reference to the dose table, and
   wherein the radiation irradiation unit is an unit that irradiates the breast with radiation under the irradiation condition set by the irradiation condition setting unit.

2. The radiographic imaging device according to claim 1, further comprising:
   a selection unit that selects which irradiation condition of an irradiation condition matching the inside of an implant region and an irradiation condition matching the outside of the implant region is to be set with regard to the irradiation condition.

3. The radiographic imaging device according to claim 1, further comprising:
   an implant information acquisition unit that acquires implant information representing whether or not the implant is included in the breast based on the pre-radiographic image,
   wherein, in a case where the implant is included in the breast, the irradiation condition setting unit sets the irradiation condition based on the difference between the transmission dose of the mammary gland region at the time of the pre-radiographing and the calculated transmission dose with reference to the dose table as a first irradiation condition of radiation for irradiating the subject in a case where there is the implant.

4. The radiographic imaging device according to claim 2, further comprising:
   an implant information acquisition unit that acquires implant information representing whether or not the implant is included in the breast based on the pre-radiographic image,
   wherein, in a case where the implant is included in the breast, the irradiation condition setting unit sets the irradiation condition based on the difference between the transmission dose of the mammary gland region at the time of the pre-radiographing and the calculated transmission dose with reference to the dose table as a first irradiation condition of radiation for irradiating the subject in a case where there is the implant.

5. The radiographic imaging device according to claim 3,
   wherein, in a case where an implant is not included in the breast, the irradiation condition setting unit sets a second irradiation condition of radiation for irradiating the subject in a case where there is no implant.

6. The radiographic imaging device according to claim 4,
   wherein, in a case where an implant is not included in the breast, the irradiation condition setting unit sets a second irradiation condition of radiation for irradiating the subject in a case where there is no implant.

7. The radiographic imaging device according to claim 5,
   wherein the irradiation condition setting unit sets any of the first irradiation condition and the second irradiation condition according to at least one of a combination of a target generating radiation in the radiation irradiation unit and a filter capable of selectively absorbing a high energy component or a low energy component of radiation or a tube voltage and a tube current of a radiation source in the radiation irradiation unit.

8. The radiographic imaging device according to claim 6,
   wherein the irradiation condition setting unit sets any of the first irradiation condition and the second irradiation condition according to at least one of a combination of a target generating radiation in the radiation irradiation unit and a filter capable of selectively absorbing a high energy component or a low energy component of radiation or a tube voltage and a tube current of a radiation source in the radiation irradiation unit.

9. The radiographic imaging device according to claim 5,
   wherein the irradiation condition setting unit sets any of the first irradiation condition and the second irradiation condition according to an irradiation time of radiation additionally.

10. The radiographic imaging device according to claim 6,
    wherein the irradiation condition setting unit sets any of the first irradiation condition and the second irradiation condition according to an irradiation time of radiation additionally.

11. The radiographic imaging device according to claim 7,
    wherein the irradiation condition setting unit sets any of the first irradiation condition and the second irradiation condition according to an irradiation time of radiation additionally.

12. The radiographic imaging device according to claim 8,
wherein the irradiation condition setting unit sets any of the first irradiation condition and the second irradiation condition according to an irradiation time of radiation additionally.

13. The radiographic imaging device according to any one of claim 5,
wherein the first irradiation condition satisfies at least one of a condition that average energy is high, a condition that an irradiation time of radiation is short, or a condition that the irradiation dose of radiation determined by the tube voltage and the tube current is large, compared to the second irradiation condition.

14. The radiographic imaging device according to any one of claim 6,
wherein the first irradiation condition satisfies at least one of a condition that average energy is high, a condition that an irradiation time of radiation is short, or a condition that the irradiation dose of radiation determined by the tube voltage and the tube current is large, compared to the second irradiation condition.

15. The radiographic imaging device according to any one of claim 7,
wherein the first irradiation condition satisfies at least one of a condition that average energy is high, a condition that an irradiation time of radiation is short, or a condition that the irradiation dose of radiation determined by the tube voltage and the tube current is large, compared to the second irradiation condition.

16. The radiographic imaging device according to any one of claim 3, further comprising:
information acquisition setting unit that sets whether or not to acquire the implant information by the implant information acquisition unit,
wherein the irradiation condition setting unit is a unit that sets a third irradiation condition in a case where a setting for not acquiring the implant information is performed.

17. The radiographic imaging device according to any one of claim 5, further comprising:
information acquisition setting unit that sets whether or not to acquire the implant information by the implant information acquisition unit,
wherein the irradiation condition setting unit is a unit that sets a third irradiation condition in a case where a setting for not acquiring the implant information is performed.

18. The radiographic imaging device according to any one of claim 4, further comprising:
information acquisition setting unit that sets whether or not to acquire the implant information by the implant information acquisition unit,
wherein the irradiation condition setting unit is a unit that sets a third irradiation condition in a case where a setting for not acquiring the implant information is performed.

19. The radiographic imaging device according to any one of claim 6, further comprising:
information acquisition setting unit that sets whether or not to acquire the implant information by the implant information acquisition unit,
wherein the irradiation condition setting unit is a unit that sets a third irradiation condition in a case where a setting for not acquiring the implant information is performed.

20. A radiographic imaging method that is performed by the radiographic imaging device according to claim 1 which irradiates a breast as a subject with radiation and detects radiation transmitted through the breast to acquire a radiographic image of the breast, the radiographic imaging method comprising:
allowing the irradiation condition setting unit, in setting the irradiation condition of radiation for irradiating the breast in acquiring the radiographic image,
to calculate the thickness of the breast,
to calculate the transmission dose based on the calculated thickness of the breast with reference to a dose table for setting the transmission dose according to the thickness of the breast,
to analyze a pre-radiographic image acquired by performing pre-radiographing for irradiating the breast with a small dose of radiation, before the radiographic image is acquired by irradiating the breast with radiation under the irradiation condition set by the irradiation condition setting unit, to recognize the implant region corresponding to the implant included in the breast in the pre-radiographic image,
to extract the mammary gland region from the region excluding the implant region in the pre-radiographic image,
to calculate the transmission dose of the mammary gland region at the time of the pre-radiographing from the pixel value of the mammary gland region, and
to set the irradiation condition based on the difference between the dose of transmitted radiation of the mammary gland region at the time of the pre-radiographing and the calculated transmission dose with reference to the dose table, and
allowing the radiation irradiation unit to irradiate the breast with radiation under the irradiation condition set by the irradiation condition setting unit.

* * * * *